US00PP32010P2

(12) United States Plant Patent
Griffin

(10) Patent No.: US PP32,010 P2
(45) Date of Patent: Jul. 21, 2020

(54) ***ALOE* PLANT NAMED 'SWORDFISH'**

(50) Latin Name: *Aloe hybrida*
Varietal Denomination: SWORDFISH

(71) Applicant: Kelly Griffin, Carlsbad, CA (US)

(72) Inventor: Kelly Griffin, Carlsbad, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 16/501,151

(22) Filed: Feb. 26, 2019

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Aloe* cultivar named 'SWORDFISH' is disclosed, characterized by violet-blue leaves with a scalloped red edge. Plants are a size suitable for landscape use. The new variety is an *Aloe*, typically produced as a garden or container plant.

2 Drawing Sheets

Figure 1:
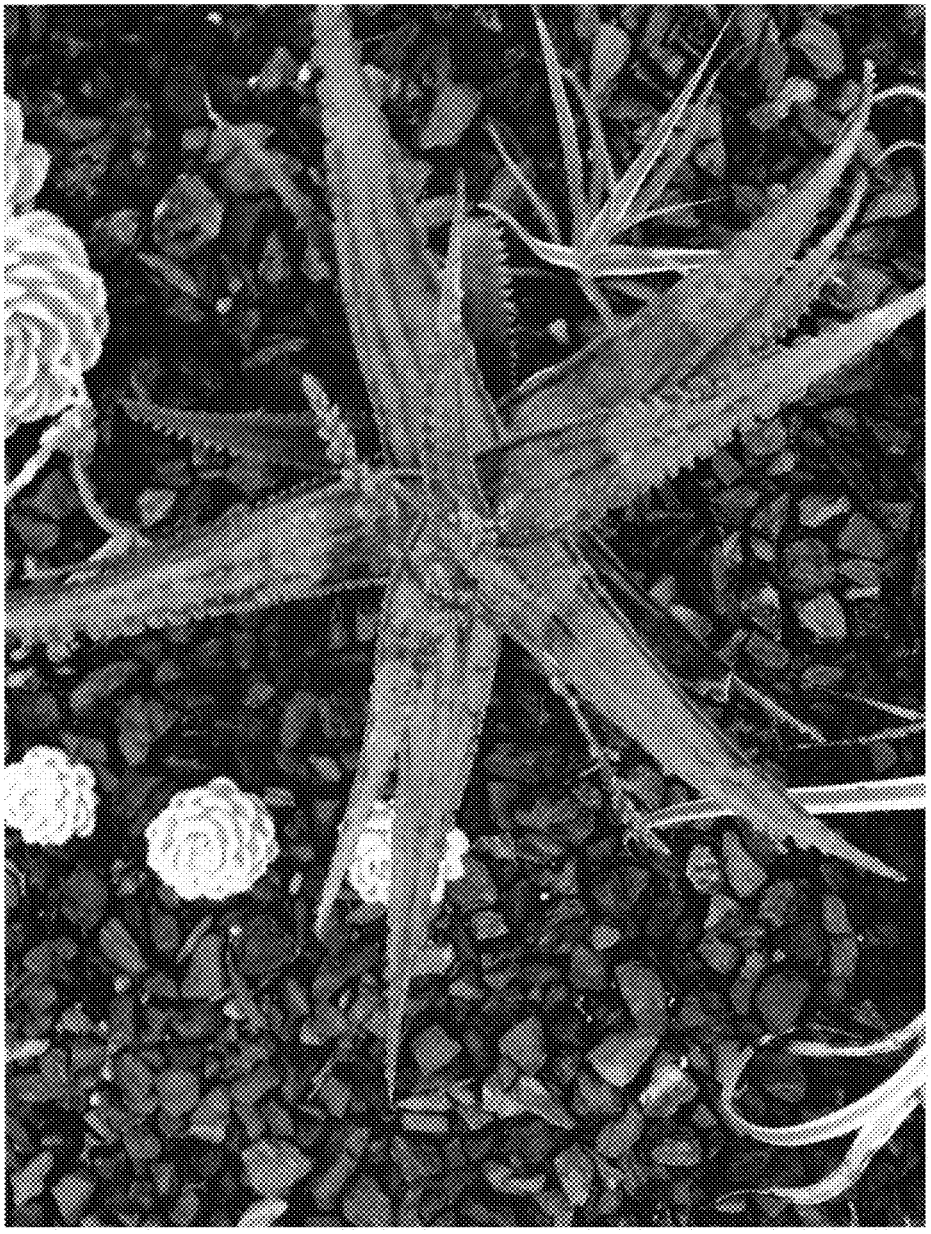

Latin name of the genus and species: *Aloe hybrida*.
Variety denomination: 'SWORDFISH'.

BACKGROUND OF THE INVENTION

The new cultivar is a product of a planned breeding program. The seed parent is the unpatented *Aloe* hybrid 'Sunset'. The pollen parent is an unnamed, unpatented variety of *Aloe divaricata*. The crossing was made in December 2014 at a commercial greenhouse in Vista, Calif. 'SWORDFISH' was selected by the inventor in November 2015.

Asexual reproduction of the new cultivar 'SWORDFISH' was first performed by tissue culture at a commercial laboratory in Vista, Calif. in December 2015. 'SWORDFISH' has since produced several generations and has shown that the unique features of this cultivar are stable and reproduced true to type.

SUMMARY OF THE INVENTION

The cultivar 'SWORDFISH' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SWORDFISH.' These characteristics in combination distinguish 'SWORDFISH' as a new and distinct *Aloe* cultivar:

1. Scalloped red leaf edge.
2. Intense violet-blue leaves.
3. Branched red-flowered inflorescence.
4. Larger plant size suitable for landscape use.

PARENTAL COMPARISON

Plants of the new cultivar 'SWORDFISH' are similar to the seed parent in most horticultural characteristics. However, plants of the new variety differ from the seed parent in the following:

1. New variety is a larger plant than the seed parent.
2. New variety has brighter colored leaves than the seed parent.
3. New variety has a deeper red and more pronounced leaf edge than the seed parent.
4. New variety produces larger flowers than the seed parent.

Plants of the new cultivar 'SWORDFISH' are similar to the pollen parent in most horticultural characteristics. However, plants of the new variety differ in the following:

1. New variety is a smaller plant than the pollen parent.
2. New variety has a more violet-blue leaf color than the pollen parent.
3. New variety has a more distinct scalloped leave edge than the pollen parent.

COMMERCIAL COMPARISON

'SWORDFISH' can be compared to the unpatented commercial variety *Aloe* 'Sunset'. The two *Aloe* varieties are similar in most horticultural characteristics; however, the new variety differs in the following:

1. New variety is a larger plant than this comparator.
2. New variety has more colorful leaves than this comparator.
3. New variety has larger flowers than this comparator.

'SWORDFISH' can also be compared to the commercial variety *Aloe* 'Candy Corn' (unpatented). The two *Aloe* varieties are similar in most horticultural characteristics; however, the new variety differs in the following:

1. New variety has better symmetry than this comparator, with foliage growing at more regular spacing.
2. New variety has brighter coloring of leaves at all light levels than this comparator.
3. New variety has more clearly defined red scalloped edges than this comparator.

BRIEF DESCRIPTION OF THE PHOTOGRAPHS

The accompanying photograph in FIG. 1 illustrates in full color a typical flowering plant of 'SWORDFISH' grown outdoors in Carlsbad, Calif. This plant is approximately 2 years old.

Figure 2:
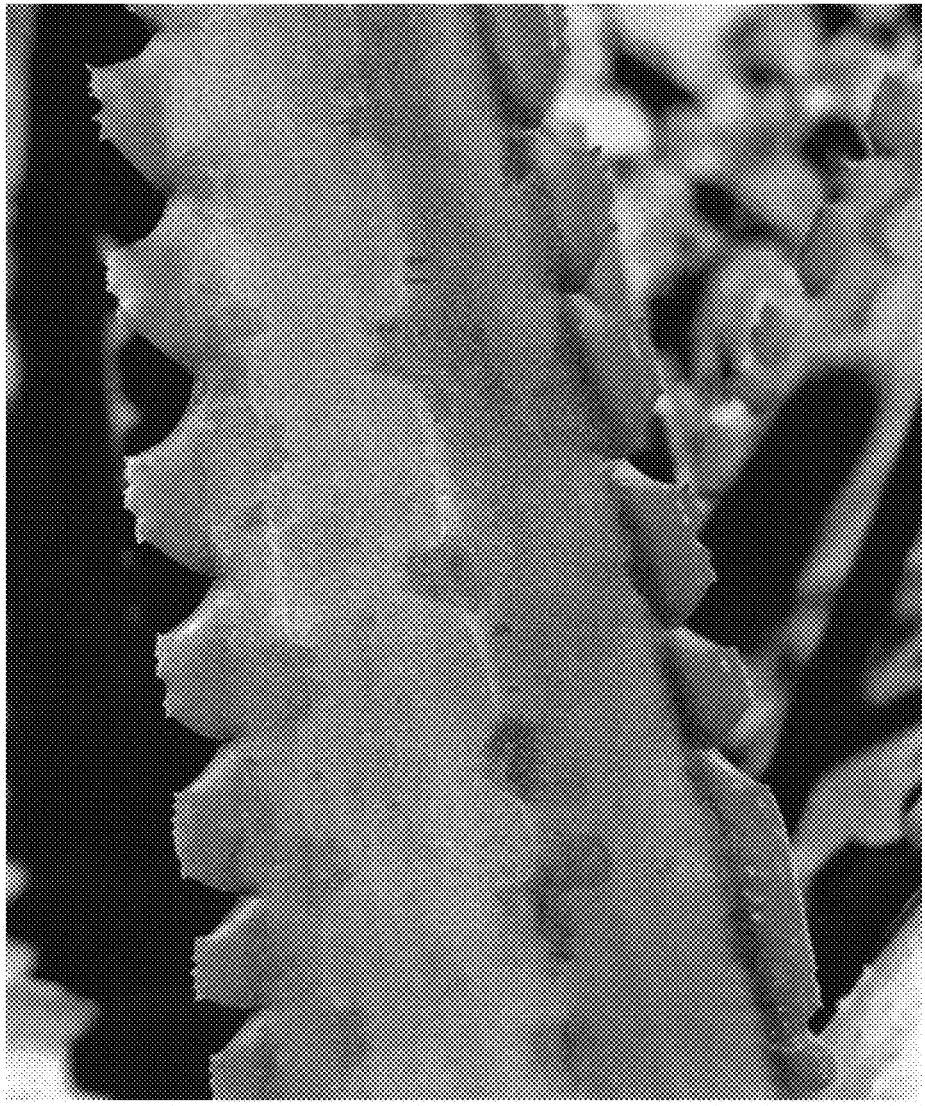

FIG. 2 illustrates a close up view of the upperside of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Color Chart, 2007 edition, except where general terms of ordinary dictionary significance are used. The following observations and measurements describe 'SWORDFISH' plants in a commercial greenhouse in Vista, Calif. Temperatures ranged from 21° C. to 25° C. during the day, and 18° C. to 21° C. during the night. No artificial light, photoperiodic treatments or chemical treatments were given to the plants. Natural light conditions were approximately 2500 to 3000 fc of light. Measurements and numerical values represent averages of typical plant types.

Botanical classification: *Aloe hybrida* 'SWORDFISH.'.

Age of the plant described: 2 years.

PROPAGATION

Time to initiate roots: Approximately 25 days at 22° C.

Root description: Fibrous. Brown, not accurately measured with The R.H.S. chart.

Propagation method: Vegetative divisions or tissue culture.

PLANT

Growth habit: Upright rosette, offsetting to form clumps with time.

Container size: 1 gallon.

Height: Approximately 28 cm to top of highest leaf. Approximately 52 cm to top of highest inflorescence.

Plant spread: Approximately 45 cm.

Growth rate: Moderate.

Branching characteristics: Offsets from base of plant.

FOLIAGE

Leaf:

*Arrangement*.—Rosette.

*Average length*.—25-28 cm.

*Average width*.—4-6 cm.

*Shape of blade*.—Lanceolate, slightly deltoid.

*Apex*.—Slightly rounded.

*Base*.—Clasping.

*Margin*.—Scalloped.

*Texture of top surface*.—Smooth.

*Texture of bottom surface*.—Smooth.

*Quantity of leaves*.—Approximately 10 to 15.

*Color*.—Young foliage upper side: Near RHS Greyed-Green 191A with glaucous layer near Blue-Green 122C. Scalloped margin near Red 41A. Young foliage under side: Near RHS Green N138C with glaucous layer near Blue-Green 122C. Scalloped margin Red 41A. Mature foliage upper side: Near Green N138B, Thick flush, strongest along margin near Greyed-Purple 183A. Overall Glaucous layer near Greyed-Green 191D. Scalloped margin Red 42B. Mature foliage under side: Near Green N138B, Thick flush, strongest along margin near Greyed-Purple 183A. Overall Glaucous layer near Greyed-Green 191D. Scalloped margin Red 42C.

*Venation*.—Linear. Color: Indistinguishable from leaf blade.

FLOWER

Natural flowering season: Intermittently throughout the year in Southern California. 3 to 4 times per year.

Inflorescence type and habit: Branched open panicle.

Rate of flower opening: Moderate, successive.

Flower longevity on plant: 1.5 months.

Quantity of flowers: 30 to 50 on average.

Total inflorescence size:

*Height*.—Approximately 45 cm.

*Width*.—Approximately 35 cm.

Flower bud:

*Shape*.—Cylindrical.

*Length*.—Approximately 2.5 cm.

*Diameter*.—Approximately 0.5 cm.

*Color*.—Near Red 42B.

Corolla:

*Arrangement*.—Perianth cylindrical/corolla small and reflexed.

*Length*.—Approximately 2.5 cm.

*Width*.—Approximately 1.0 cm at widest point.

*Color, upper side*.—RHS Red 42C.

*Color, under side*.—RHS Red 42D.

Calyx:

*Shape*.—Tubular.

*Length*.—2.4 cm.

*Diameter*.—0.8 cm horizontal; 0.75 cm vertical.

*Color, upper side*.—RHS Greyed-Orange 170D.

*Color, under side*.—RHS Greyed-Orange 170D.

Pedicel:

*Length*.—Approximately 1 cm.

*Width*.—0.2 cm.

*Aspect*.—Lateral.

*Color*.—Near Green 138C flushed Red 42C.

Fragrance: None.

REPRODUCTIVE ORGANS

Stamens:

*Number*.—6.

*Filament length*.—2.5 cm.

*Filament color*.—White 155D.

*Anther length*.—0.25 cm.

*Anther color*.—Yellow 7A.

*Anther shape*.—Oval.

*Pollen color*.—Yellow 7A.

Pistil:

*Number*.—1.

*Length*.—Approximately 3 cm.

*Style color*.—White 155D.

*Stigma*.—Shape: Rounded. Color: White 155D. Ovary color: Green 138D.

OTHER CHARACTERISTICS

Seeds and fruits: Not observed to date.

Temperature tolerance: Tolerates temperatures from approximately 28° C. to 0° C.

Disease/pest resistance: Shows mite resistance and black spot resistance.

What is claimed is:

1. A new and distinct cultivar of *Aloe* plant named 'SWORDFISH' as herein illustrated and described.

* * * * *